(12) United States Patent
Stohs et al.

(10) Patent No.: US 8,975,236 B2
(45) Date of Patent: Mar. 10, 2015

(54) DIETARY SUPPLEMENT COMPOSITION OF CITRUS DERIVATIVES

(76) Inventors: Sidney J. Stohs, Frisco, TX (US); Howard Miller, Secaucus, NJ (US)

(*) Notice: Subject to any disclaimer, the term of this patent is extended or adjusted under 35 U.S.C. 154(b) by 543 days.

(21) Appl. No.: 13/159,400

(22) Filed: Jun. 13, 2011

(65) Prior Publication Data
US 2012/0316123 A1    Dec. 13, 2012

(51) Int. Cl.
 *A61K 31/137* (2006.01)
 *A61K 31/352* (2006.01)
 *A61K 31/7048* (2006.01)

(52) U.S. Cl.
 CPC .............. *A61K 31/137* (2013.01); *A61K 31/352* (2013.01); *A61K 31/7048* (2013.01)
 USPC .............................. 514/27; 514/453; 514/456

(58) Field of Classification Search
 CPC ............ A61K 2300/00; A61K 31/137; A61K 31/352; A61K 31/7048
 USPC ............................................ 514/27, 453, 456
 See application file for complete search history.

(56) References Cited

U.S. PATENT DOCUMENTS

2009/0118359 A1*  5/2009  Brunia et al. ................. 514/456

OTHER PUBLICATIONS

Sidney J. Stohs, et al., "Effects of p-Synephrine alone and in Combination with Selected Bioflavonoids on Resting Metabolism, Blood Pressure, Heart Rate and Self-Reported Mood Changes," 8 Int'l. J. Med. Sci. 295 (2011), 12 pages.

* cited by examiner

*Primary Examiner* — Patrick Lewis
*Assistant Examiner* — Everett White
(74) *Attorney, Agent, or Firm* — Chernoff, Villhauer, McClung & Stenzel, LLP

(57) ABSTRACT

There is disclosed a dietary supplement composition of alkaloids and flavonoids extracted from citrus fruits that exhibits lipolytic and thermogenic activity and increases RMR, while at the same time exhibiting no negative side effects such as increase in blood pressure or heart rate. The composition essentially comprises two components: (A) the protoalkaloids synephrine, tyramine, N-methyltyramine, hordenine and octopamine; and (B) at least one of hesperidin, naringin and mixtures thereof.

7 Claims, 3 Drawing Sheets

Hesperidin

Naringin

Hesperidin

Naringin

DIETARY SUPPLEMENT COMPOSITION OF CITRUS DERIVATIVES

BACKGROUND OF THE INVENTION

A commercially available dietary supplement sold as Advantra Z® contains the protoalkaloids synephrine, tyramine, N-methyltyramine, hordenine and octopamine, with synephrine being the main ingredient. The makers of Advantra Z® claim that the composition shows lipolytic and thermogenic activity and increases resting metabolic rate (RMR) in humans, with synephrine and octopamine appearing to be particularly effective in this regard. Such properties have value in treatment of weight loss and in improving both physical performance and overall fitness.

The flavonoids hesperitin and naringenin are found in citrus fruits and juices as their glycosides, hesperidin and naringin, respectively. Hesperidin is present predominantly in the peels of lemons and oranges as well as in a wide variety of other citrus species, while naringin is mainly found in the peels of grapefruit. Both flavonoids are commercially readily available in the form of powders, tablets, capsules and the like. The sugar moieties for rutinose (rhamnose and glucose) of these flavonoids must be cleaved to enable the flavonoids to be absorbed; typically this cleavage occurs naturally in the GI tract of a human or mammal. Experiments involving human subjects, animals and cell culture systems have shown that naringin and hesperidin exhibit a wide range of potentially beneficial physiological and biochemical effects. However, no studies have been conducted on the effects of either flavonoid on metabolic rate, blood pressure or heart rate.

BRIEF SUMMARY OF THE INVENTION

According to the present invention, there is provided a dietary supplement composition of *Citrus* derivatives comprising the components: (A) the protoalkaloids of Advantra Z®, namely, synephrine, tyramine, N-methyltyramine, hordenine and octopamine; and (B) at least one of hesperidin, naringin and mixtures thereof. The composition provides significant improvement of the lipolytic, thermogenic and RMR effects of component (A), while at the same time exhibiting no elevation in blood pressure or heart rate.

DETAILED DESCRIPTION OF PREFERRED EMBODIMENTS

Figure 1:
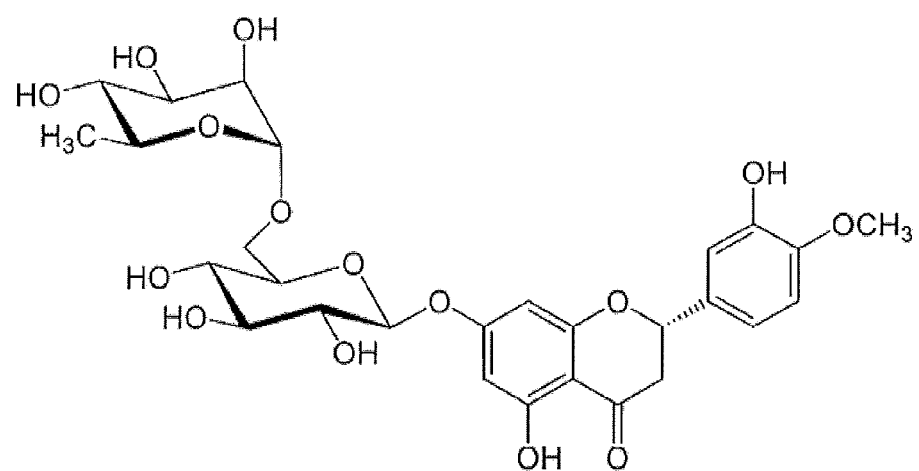
FIG. 1 Shows the chemical structures of hesperidin and naringin.
Figure 1:
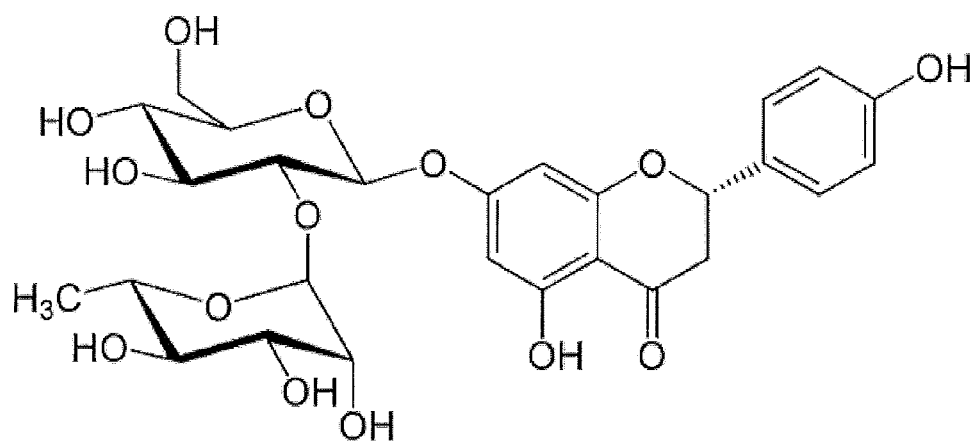

The invention lies in the discovery that the *Citrus*-derived species hesperidin and naringin, when added to the components of Advantra Z®, enhance the lypolytic, thermogenic and RMR effects of that product while causing no elevation in blood pressure or heart rate.

The composition of the invention can be administered in the form of the source plant material in a tablet, capsule or other pharmacologically acceptable carrier; in the form of a tea or energy drink; or as a tablet, capsule or other pharmacological carrier which contains (A) and (B) as described in the Brief Summary of the Invention above.

Though it is possible to use a variety of *Citrus* materials in accordance with the invention, it is more convenient and preferred to use *Citrus* materials which already exist in ingestible form and which are generally available as conventional herbs and dietary supplements. For example, the agents are present in the residues remaining after steam distillation of *Citrus aurantium* components to obtain the essential oils. In this respect, various well known Chinese herbs are particularly useful, as are *Citrus reticulata* leaves.

Preferred common Chinese herbs include Zhi shi, which is the immature dried fruit of *Citrus aurantium*, but may also consist of the peel of the mature fruit, or the peel of either. This herb contains 0.2-0.9 wt % total protoalkaloids, with synephrine predominating; Zhi Qiao, also the immature fruit of *Citrus aurantium*, and which has similar levels of actives as Zhi shi; Chen pi or Jiu Hong, the dried peel of *Citrus reticulata* containing 0.1-0.4 wt % total alkaloids; Qing pi, the dried immature fruit of *Citrus reticulata*, containing 0.1-0.4 wt % total alkaloids; and Fo Shou, also known as *Fructus Citri Sarcodactyli*, the fruit of *Citrus medica* var. *sarcodactylus*, containing 0.1-0.3 wt % total alkaloids. In addition, peel of the mature or immature fruit of *Citrus limon* (lemon) and *Citrus tangerina* (tangerine) leaves are useful, since the former is commercially available while tangerine leaves are available in season.

The composition of the invention can be administered to humans orally, either with or without caloric restriction for controlling body weight. The composition works predominantly by increasing thermogenesis, that is, by increasing metabolic rate and facilitating lipolysis. The composition also increase metabolism of carbohydrates to produce energy by stimulating the production of adenosine triphosphate. In addition, ingestion of the composition causes a hunger-suppressing effect which may become more obvious in higher doses. Thus, most users will benefit mainly from the thermogenic effect and may also experience mild suppression of hunger so that both effects promote weight loss. In addition, the composition can be administered to humans either with or without a high protein diet (>1.25 g protein/kg ideal body weight/day), for the purpose of increasing physical performance in the short-term and to increase muscle mass in the long term.

In a preferred embodiment, an appropriate dose of the composition is at least 1.0 mg of actives per kg ideal body weight, with four doses per day. In practical terms this corresponds to a dose of 70 mg for a person whose ideal body weight is 70 kg, or 280 mg per day. More preferably, the dose is in the range of 1.0 to 20 mg actives per kg of ideal body weight per serving, even more preferred is a range of 7 to 13 mg actives per kg of ideal body weight, and most preferred is 11 mg actives per kg of ideal body weight. Through larger doses of the composition will not diminish the beneficial effects, the effects may not necessarily be increased while the possibility of side-effects due to activation of other adrenergic systems may be increased.

The composition of the invention may be consumed as a concentrate or as an extract in either dry or liquid form. Concentrates and extracts may be prepared by conventional methods known in the pharmaceutical arts, such as by extraction of the components of the composition with water, dilute acids, organic solvents, and mixtures thereof, followed by drying on a carrier of unconcentrated *Citrus* material, or by drying on a carrier of another suitable material. Such conventional methods are disclosed in, for example, Avula et al., 88 *JAOAC Int.* 1593 (2005); Nelson et al., 55 *J. Agric. Food Chem.* 9679 (2007); and Lopez et al., 30 *Crit. Rev. Biotech.* 63 (2010). Suitable carriers include, but are not limited to, maltodextrins, starch or protein. The composition components may also be extracted and concentrated without drying to yield a liquid extract.

In a preferred embodiment, when prepared as an extract or concentrated, the components are preferably dried so that the composition may be administered in the form of tablets, capsules, powders or other convenient form, or it may be admixed with foods or special food products, or it may be given in the form of a tea or tisane. When prepared as a liquid extract, the *Citrus* material may be administered as drops, or from an appropriate liquid measure such as a teaspoon, or it may be admixed with other liquids.

The composition of the invention may also be incorporated into other food products, such as a nutritional drink or nutritional bar. As an example, a nutritional bar may provide 16 grams of protein, 21 grams of carbohydrate and 7 grams of fat in addition to the composition. Such products may be used as meal replacements by one seeking weight loss, or by those requiring nutritional support during sporting activities.

The composition may also be given in combination with other herbs either separately or in admixture that possess beneficial effects for humans, and particularly in respect to weight loss or improvements in physical performance. In this connection, suitable herbs and foods include those that contain methylxanthines such as caffeine, theobromine and theophylline, which by virtue of their inhibition of the enzyme phosphodiesterase, may potentiate the thermogenic actions of the *Citrus* materials and increase the actions at the level of the beta-3-adrenoreceptors in adipose tissue. At the same time, the action of synephrine on beta-3-adrenoreceptors in cardiovascular tissues may serve to reduce or eliminate any unwanted cardiovascular effects, such as peripheral vasoconstriction and increase in blood pressure associated with methylxanthines that would be undesirable in the context of weight loss or improved physical performance. Suitable methylxanthine-containing substances include, but are not limited to, *Paullinia cupana* (Guarana), *Llex paraguariensis* (Mate), *Cola nitida, Cola acuminata, Camellia sinensis* (Tea), *Coffea arabica* (Coffee) and *Theobroma cacao* (Cocoa), and may be used as the natural material or as an extract thereof.

EXAMPLE

A study was designed to examine the effects of Advantra Z® with various amounts of hesperidin and naringin on: (1) resting metabolic rate (RMR); (2) blood pressure; (3) resting heart rate; and (4) self-reported mood/energy levels in 50 healthy human subjects. The study used a double-blind, randomized, placebo-controlled protocol. More specifically, the participants fasted for 8-10 hours without consuming caffeinated beverages, nicotine, exercising or participating in vigorous physical activities. Upon reporting to the research center, participants completed the 10-item questionnaire in Table 1.

TABLE 1

Rating Scale Completed by Participants at Baseline and 45 and 75 Minutes from Baseline

| | | | |
|---|---|---|---|
| Energy level | Very Low | 1...2...3...4...5 | Very High |
| Hunger Level | Very Low | 1...2...3...4...5 | Very High |
| Concentration | Very Low | 1...2...3...4...5 | Very High |
| Sleepiness | Very Low | 1...2...3...4...5 | Very High |
| Upset stomach | Very Low | 1...2...3...4...5 | Very High |
| Headache | Very Low | 1...2...3...4...5 | Very High |
| Nervousness | Very Low | 1...2...3...4...5 | Very High |
| Overall anxiety | Very Low | 1...2...3...4...5 | Very High |
| Overall tension | Very Low | 1...2...3...4...5 | Very High |
| General discomfort | Very Low | 1...2...3...4...5 | Very High |

Measurements of participants' blood pressure and resting heart rate were taken by conventional methods, while RMR was measured by a MedGem® Indirect calorimeter from Microlife Medical Home Solutions of Golden, Colo. Test-retest reliabilities were measured on 41 of the 50 participants in test-retest periods ranging 1-17 days between tests. As shown in Table 2, the average reliability coefficient was 92%.

TABLE 2

Test-retest Reliabilities for RMR Measurements

| Time Period | # Days | Coefficient |
|---|---|---|
| All days (0-14) | 41 | 89% |
| Same day | 10 | 89% |
| 1-6 days | 11 | 97% |
| 7-10 days | 10 | 89% |
| 11-17 days | 10 | 97% |

Standard samples containing 50 mg p-synephrine were of powdered Advantra Z® assayed for p-synephrine content and mixed into one-ounce portions of V-8® juice for the tests. Following RMR measurements, participants were randomly assigned to one of five groups of 10 each in which each participant consumed one ounce of V-8® juice containing the following ingredient variations:

Group 1: Placebo (V-8® juice only);
Group 2: 50 mg p-synephrine*;
Group 3: 50 mg p-synephrine* with 1,000 mg hesperidin and 600 mg naringin;
Group 4: 50 mg p-synephrine* with 600 mg naringin; and
Group 5: 50 mg p-synephrine* with 100 mg hesperidin and 600 mg naringin.

*in Advantra Z® containing minor amounts of the protoalkaloids tyramine, N-methyl tyramine, hordenine and octopamine After resting for 45 and 75 minutes, participants completed a second and a third questionnaire. After 75 minutes, measurements of blood pressure, heart rate and RMR were taken. RMR measurements were taken with a MicroLife MedGen indirect calorimeter that measures oxygen consumed and converts it into kcal.

Figure 2:
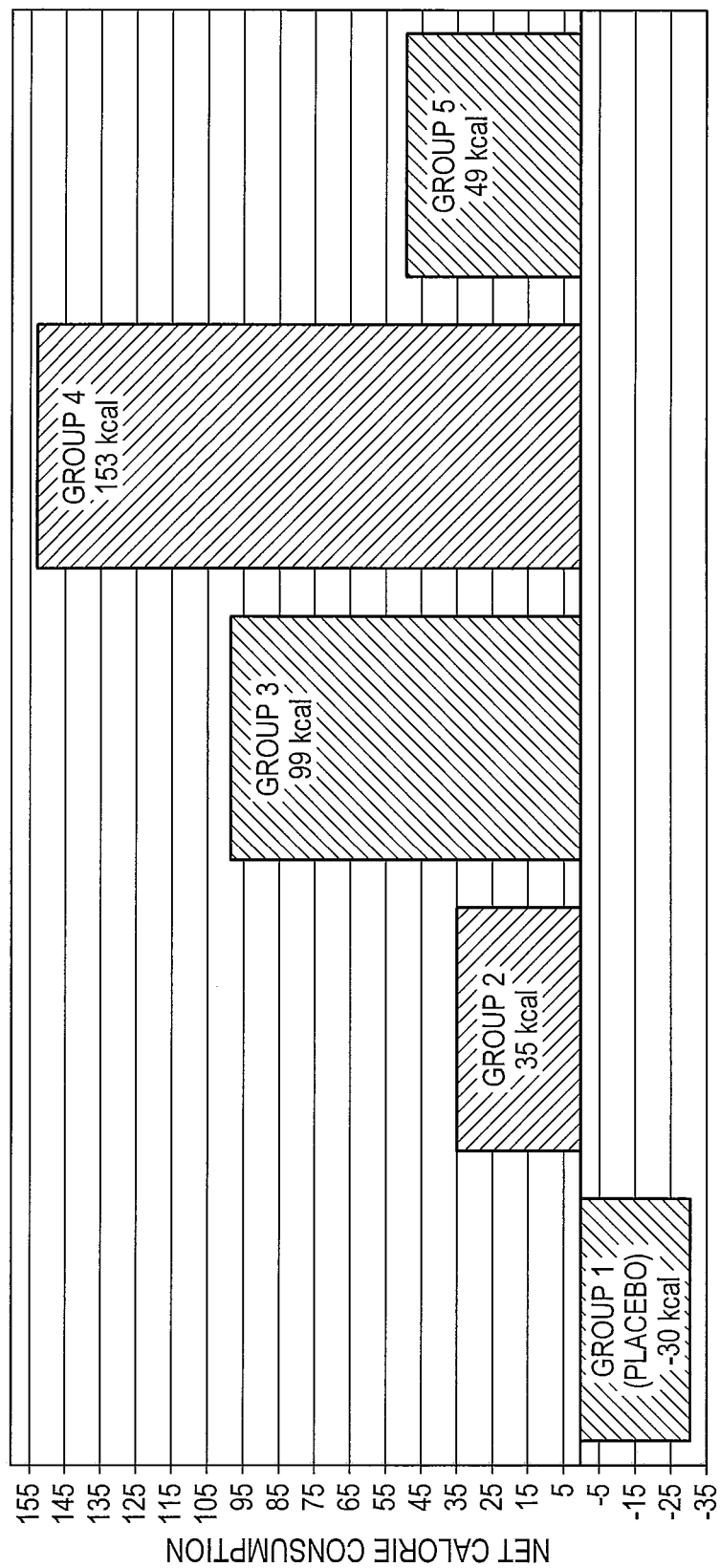
FIGS. 2-3 Comprise graphical representations of RMR and projected annual weight loss, respectively, of patients taking compositions of the invention.

FIG. 2 shows changes in RMR for the subjects in each of the five treatment groups. Group 1 (the placebo group) exhibited a 2.2% decrease in RMR which is expected since the subjects had consumed no food after an overnight fast (due to lack of caloric intake the metabolic rate decreased). The metabolic rate of Group 2 (the Advantra Z® only group) increased by 4.7%, showing a net increase of 6.9% in RMR relative to Group 1. For Group 3, the RMR increased 7.6% relative to Group 1, while for group 5, the RMR increased by 12.2%. The greatest increase in RMR (17.7%) occurred when subjects consumed Advantra Z® with 100 mg hesperidin and 600 mg naringin (Group 4).

Figure 3:
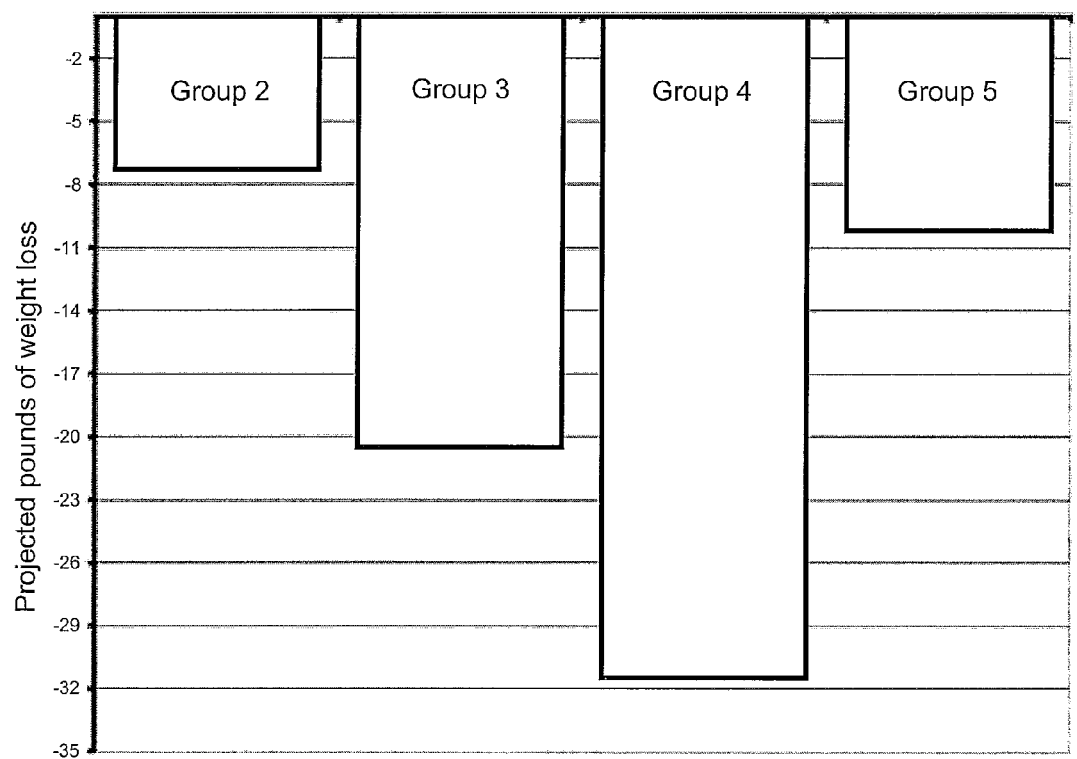

FIG. 3 is a graphical illustration of extrapolation of results of the study in terms of the estimated weight loss for subjects taking two doses a day of four supplements containing Advantra Z® alone or in combination with hesperidin and/or naringin for one year. Subjects dosed with ~50 mg Advantra Z® only would be projected to lose an average of 7 lbs, while those dosed with ~50 mg Advantra Z®, 1 g hesperidin and 600 mg naringin would be projected to lose an average of about 10 lbs. Subjects dosed with ~50 mg Advantra Z® with 100 mg hesperidin and 600 mg naringin would be projected to lose an average of about 32 lbs., while those dosed with ~50 mg Advantra Z® with no hesperidin and 600 mg naringin would lose a projected average of about 20 lbs.

Table 3 shows changes in blood pressure and resting heart rate from baseline to the last test for each of the five study groups, and includes P (or probability) Values. The average baseline blood pressures and resting heart rates for the study cohort were well within the normal range of 121/74 and 70 BPM, respectively. As indicated by the low P Values, none of the baseline-ending changes approached statistical significance nor were there any statistically significant differences between any of the five study groups.

TABLE 3

Baseline and Ending Blood Pressures and Resting Heart Rates for the 5 Groups With P Values for Baseline-Ending Within-Groups

| Grp | Baseline | | | Ending | | | Chg & P Value | | Chg & P Value | | Chg & P Value | |
| | SYS-1 | DIA-1 | HR-1 | SYS-2 | DIA-2 | HR-2 | SYS | P | DIA | P | HR | P |
|---|---|---|---|---|---|---|---|---|---|---|---|---|
| 1 | 123 | 71 | 65 | 123 | 75 | 63 | 0.4 | 0.84 | 3.7 | 0.29 | −1.8 | 0.28 |
| 2 | 121 | 74 | 72 | 120 | 75 | 72 | −0.2 | 0.95 | 0.9 | 0.68 | −0.6 | 0.79 |
| 3 | 126 | 77 | 69 | 131 | 75 | 68 | 5.2 | 0.19 | −1.6 | 0.39 | −1.4 | 0.42 |
| 4 | 120 | 77 | 70 | 121 | 76 | 65 | 0.9 | 0.76 | −1.5 | 0.32 | −4.8 | 0.11 |
| 5 | 118 | 73 | 72 | 119 | 72 | 69 | 1.4 | 0.72 | −0.9 | 0.64 | −3.0 | 0.17 |

Table 4 provides a summary of changes in self-rating from baseline and P Values for comparisons of subjects in Groups 2-5 relative to Group 1 (the placebo group). No statistically significant changes occurred in any of the 10 self-reported symptoms at either the 45 min or the 75 min time points relative to baseline. Consumption of the product formulations did not produce any adverse effects such as sleeplessness, inability to concentrate, nervousness, stomach upset, headache, tension or general discomfort.

placebo group and the Advantra Z® alone group. The inclusion of 100 mg hesperidin in Group 4 led to the greatest increase in RMR. There was a decrease in RMR in Group 5, as compared to Group 4, suggesting that increasing the hesperidin from 100 mg to 1,000 mg reversed some of the thermogenic effects of hesperidin found with ingestion of 100 mg. Similar results are expected for similar doses of Advantra Z® and naringin as for the results for the above doses of Advantra Z® and hesperidin.

Similar unexpected findings were evident with respect to the mid- and ending changes in self-reported thermogenic side effects, as shown in Tables 2 and 4. As compared to the placebo group, none of the changes in the 10 self-reported symptoms was statistically significant at either 45 or 75 minutes from baseline. This finding not only supports the absence of adverse side effects in blood pressure and resting heart rate, but validates the blinding protocol used in the study.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

TABLE 4

Mean Changes from Baseline in Each Rating for Placebo and Each Treatment Group with P Values for Between Groups Comparisons Between Placebo and Treatment Groups

| | Energy | Hunger | Concentration | Sleepiness | Upset Stomach | Headache | Nervousness | Anxiety | Tension | Discomfort | |
|---|---|---|---|---|---|---|---|---|---|---|---|
| | Mean Changes From Baseline | | | | | | | | | | |
| 1 = Placebo | 0.50 | 1.13 | −0.13 | 0.75 | 0.00 | 0.13 | −0.13 | 0.00 | −0.25 | 0.00 | 1 = Placebo |
| 2 = Advantra Z | 0.60 | 0.30 | 0.20 | 0.30 | 0.10 | 0.30 | 0.10 | 0.20 | −0.10 | 0.20 | 2 = Advantra Z |
| 3 = AZ + 600N | 0.38 | 0.00 | 0.38 | 1.00 | 0.00 | 0.00 | 0.00 | 0.00 | 0.00 | 0.00 | 3 = AZ + 600N |
| 4 = AZ + 100H, +600N | 0.75 | 0.88 | 0.25 | 0.63 | 0.13 | 0.13 | 0.00 | −0.13 | −0.38 | 0.00 | 4 = AZ + 100H, +600N |
| 5 = AZ + 1000H, +600N | 0.33 | 0.56 | 0.00 | −0.11 | 0.33 | 0.00 | 0.11 | 0.22 | 0.22 | 0.22 | 5 = AZ + 1000H, +600N |
| | P Values for Comparisons Between Placebo & Treatmet Groups | | | | | | | | | | |
| Placebo vs 2 | 0.84 | 0.21 | 0.45 | 0.40 | 0.39 | 0.52 | 0.17 | 0.20 | 0.43 | 0.39 | Placebo vs 2 |
| Placebo vs 3 | 0.71 | 0.01 | 0.35 | 0.62 | n/v | 0.33 | 0.33 | n/v | 0.15 | n/v | Placebo vs 3 |
| Placebo vs 4 | 0.51 | 0.59 | 0.40 | 0.81 | 0.33 | 1.00 | 0.33 | 0.33 | 0.69 | 1.00 | Placebo vs 4 |
| Placebo vs 5 | 0.68 | 0.29 | 0.79 | 0.09 | 0.36 | 0.57 | 0.18 | 0.36 | 0.28 | 0.36 | Placebo vs 5 |

A well known drawback to products having thermogenic properties is that they are associated with increased physiological risks from elevated blood pressure and heart rate. The absence of negative changes in blood pressure, resting heart rate and self-ratings in Groups 2-5 was therefore rather surprising and unexpected.

The following observations were made based upon the foregoing study. The inclusion of hesperidin and naringin with Advantra Z® led to increases in RMR relative to both the

The invention claimed is:

1. A composition for increasing resting metabolic rate in humans comprising the components:
   (A) 50 mg p-synephrine, protoalkaloids tyramine, N-methyl tyramine, hordenine and octopamine; and
   (B) 600 mg naringin.

2. The composition of claim 1 further comprising 100 mg hesperidin.

3. The composition of any of claim 1 or 2 in a dosage form selected from a tablet, a capsule, a powder and a liquid.

4. A method for promoting weight loss in humans comprising orally administering an effective amount of a composition comprising the components:
   (A) 50 mg p-synephrine, protoalkaloids tyramine, N-methyl tyramine, hordenine and octopamine; and
   (B) 600 mg naringin.

5. The method of claim 4 further comprising the step of administering 100 mg hesperidin.

6. A method for increasing resting metabolic rate in humans comprising orally administering an effective amount of a composition comprising the components:
   (A) 50 mg p-synephrine, protoalkaloids tyramine, N-methyl tyramine, hordenine and octopamine; and
   (B) 600 mg naringin.

7. The method of claim 6 further comprising the step of administering 100 mg hesperidin.

\* \* \* \* \*